United States Patent [19]
Jentsch et al.

[11] Patent Number: 6,005,131
[45] Date of Patent: Dec. 21, 1999

[54] MULTI-FUNCTIONAL, CYCLIC ORGANOSILOXANES, PROCESS FOR THE PRODUCTION THEREOF AND USE THEREOF

[75] Inventors: Jörg-Dietrich Jentsch, Mülheim; Michael Mager, Leverkusen; Markus Mechtel, Köln, all of Germany

[73] Assignee: Bayer Aktiengesellschaft, Leverkusen, Germany

[21] Appl. No.: 08/923,210

[22] Filed: Sep. 4, 1997

Related U.S. Application Data

[63] Continuation of application No. 08/785,463, Jan. 17, 1997, abandoned.

[30] Foreign Application Priority Data

Jan. 30, 1996 [DE] Germany .............................. 196 03 241

[51] Int. Cl.$^6$ ...................................................... C07F 7/08
[52] U.S. Cl. .............................................................. 556/434
[58] Field of Search ............................................. 556/434

[56] References Cited

U.S. PATENT DOCUMENTS

| | | |
|---|---|---|
| 4,689,085 | 8/1987 | Plueddemann . |
| 5,196,497 | 3/1993 | Weber et al. . |
| 5,200,543 | 4/1993 | Inomata et al. .......................... 556/434 |
| 5,359,109 | 10/1994 | Ritscher et al. . |
| 5,378,790 | 1/1995 | Michalczyk et al. . |
| 5,557,000 | 9/1996 | Minemura ............................... 556/434 |

FOREIGN PATENT DOCUMENTS

| | | |
|---|---|---|
| 0183533 | 6/1986 | European Pat. Off. . |
| 2234703 | 1/1973 | Germany . |

OTHER PUBLICATIONS

Chemical Abstracts, vol. 116, No. 14, Apr. 6, 1992, Columbus, Ohio, U.S.; Abstract No. 143120, A. Iwai, et al.: "Siloxane–treated packing for liquid chromatography", XP002030555, *Zusammenfassung*, *das ganze Dokument*, and JP 03 233 355 A (Dow Corning Toray Silicone Co., Ltd.; Japan), Oct. 17, 1991.

J. Organomet. Chem. (Jorcai 0022328X); 96; vol. 521 (1–2); pp. 261–266, Central Research and Development, Dupont Science and Engineering Laboratories, P.O. Box 80323; Wilmington; 19880–0323; DE; U.S.A. (U.S.), XP002030554.

M.J. Michalczyk, et al.: "Characterization of polyfunctional alkoxysilanes using potassium (K+) ionization of desorbed species mass spectrometry", *das ganze Dokument*, (1996).

A.V. Gorskov, et al., The effect of oligoalkoxysiloxanes on the properties of SRTV–M vulcanizates[1], Translation of a German translation of a Russian article, published since 1927.

D. Seyferth, et al., Synthesis of an Organosilicon Dendrimer Containing 324 Si–H Bonds, Organometallics, vol. 13, No. 7, pp. 2682–2690, (1994).

J.L. Speier, Homogeneous Catalysis of Hydrosilation by Transition Metals, Advances in Organometallic Chemistry, vol. 17, pp. 407–409, (1979).

L–L. Zhou, et al., Synthesis of Novel Carbosilane Dendritic Macromolecules[†], Macromolecules, vol. 26, No. 5, pp. 963–968, (1993).

*Primary Examiner*—Paul F. Shaver
*Attorney, Agent, or Firm*—Sprung Kramer Schaefer & Briscoe

[57] ABSTRACT

The present invention relates to novel multi-functional, cyclic organosiloxanes, to a process for the production thereof and to the use thereof.

11 Claims, No Drawings

MULTI-FUNCTIONAL, CYCLIC ORGANOSILOXANES, PROCESS FOR THE PRODUCTION THEREOF AND USE THEREOF

This application is a continuation of application Ser. No. 08/785,463, filed on Jan. 17, 1997, now abandoned.

The present invention relates to novel multi-functional, cyclic organosiloxanes, to a process for their production and to their use.

As may be learned from DE-A-4022661, linear, multi-functional silanes and siloxanes are used as crosslinking agents in condensation-crosslinking organopolysiloxane compositions, such as for example 1- and 2-component silicone pastes which cure at room temperature in the presence of moisture to yield elastomers. These compounds are also used in the production of surface coating compositions and for the modification thereof.

U.S. Pat. No. 5 359 109 describes cyclic siloxanes which are used inter alia for surface coating concrete and as a lacquer additive for paints for metal surfaces. However, these siloxanes have only one hydrolyzable group per molecule and are thus not suitable as network forming agents.

Trialkoxy-functional cyclosilanes are already known from WO 94/06807. However, these compounds have only a limited storage life as, in the presence of water, the alkoxy groups undergo slow hydrolysis and condensation to yield polymeric siloxanes. Production using the method known from the literature of hydrosilylation of trialkoxysilanes on alkenylsilanes in the presence of homogeneous catalysts yields sometimes considerable quantities of secondary products due to incomplete conversion. These secondary products may be separated only by using elaborate methods, since the principal products cannot be purified by distillation, crystallisation or other usual methods. Homogeneously catalyzed hydrosilylations moreover often exhibit the disadvantage that the heat of reaction can be controlled only with difficulty. This becomes particularly evident when it is attempted to transfer reactions from the laboratory scale to the industrial scale.

Thus, for example, the reactions of tetravinylsilane with $HSiCl_3$, $HSiCl_2Me$ or $HSiClMe_2$, in each of which four Si—C bonds are formed, are all strongly exothermic. As described in *Macromolecules* 1993, 26, 963–968, it is often necessary, even with batches of only a few grams, to cool the reaction vessel with a cooling bath, as a reflux condenser alone is not capable of recondensing the low-boiling chlorosilane.

In addition to the evolution of large quantities of heat, it is furthermore very difficult to estimate exactly when the reaction starts. If all the educts are very thoroughly purified and the catalyst freshly prepared immediately before the reaction, the reaction sometimes starts by itself without additional heating. However, in most cases, the introduction of heat is required. When the reaction does start, the preheated mixture is then all the more difficult to bring under control, for example by cooling. Possible causes could be traces of contaminants in the educts (water, HCl) and altered catalyst activity.

In *Adv. Organometallic Chem.* 1979, 17, 407–409 this behavior is described as an "induction period" and is attributed to the formation of a species which is actually catalytically active during this "induction period".

A reaction having such an unpredictable course is unfavorable for use on an industrial scale. The rapid dissipation of heat once the exothermic reaction has begun can be achieved, if at all, only with great technical difficulty.

Another disadvantage of homogeneous catalysis is that the catalyst remains in the product, even if only at a low concentration. Apart from the fact that valuable noble metal is lost, incorporation of the catalyst has generally negative effects on the subsequent products.

The object of the present invention was accordingly to provide storage-stable, multi-functional, cyclic organosiloxanes which are suitable as crosslinking agents in condensation-crosslinking organopolysiloxane compositions, such as for example 1- and 2-component silicone pastes which cure at room temperature in the presence of moisture to yield elastomers, for the production of surface coating compositions and for the modification thereof and to provide a process which does not exhibit the above-stated disadvantages.

Surprisingly, cyclic multi-functional organosiloxanes which fulfil these requirements have now been found.

The present invention accordingly provides multi-functional, cyclic organosiloxanes of the formula (I),

wherein m=3–6, preferably 3–4, n=2–10, preferably 2–5, particularly preferably 2, R=$C_1$–$C_8$ alkyl and/or $C_6$–$C_{14}$ aryl, preferably $C_1$–$C_2$ alkyl, wherein, within the molecule each individual n and R may be identical to or different than each other individual n and R, preferably identical, and, wherein the remaining residues have the following meaning:

A)
X=halogen, i.e. Cl, Br, I and F, preferably Cl and a=1–3 or X=OR' or OH and a=1–2, wherein R'=$C_1$–$C_8$ alkyl, preferably $C_1$–$C_2$ alkyl, or B)
X=[$(CH_2)_nSiY_bR_{3-b}$], a=1–3 and b=1–3,
Y=halogen, OR' or OH, preferably Cl, OR', OH, wherein R'=$C_1$–$C_8$ alkyl, preferably $C_1$–$C_2$ alkyl, or C)
X=[$(CH_2)_nSiR_{3-b}[(CH_2)_nSiY_cR_{3-c}]_b$] wherein, a=1–3, b=1–3 and c=1–3,
Y=halogen, OR' or OH, preferably Cl, OR', OH, wherein R'=$C_1$–$C_8$-alkyl, preferably $C_1$–$C_2$ alkyl.

In formula (I), R, and R' represent $C_1$–$C_8$ alkyl and/or $C_6$–$C_{14}$ aryl. Representative $C_1$–$C_8$ alkyl groups include, but are not limited to, methyl, ethyl, iso-propyl, n-propyl, n-heptyl, n-octyl, 2-ethyl hexyl, although methyl and ethyl are preferred and methyl is particularly preferred. Representative $C_6$–$C_{14}$ aryl groups include, but are not limited to, phenyl, tolyl, benzyl, naphthyl, although phenyl is preferred. The aryl groups may be substituted rings. Substituents include, but not limited to, Cl, Br, amine, nitro- or sulfonato- groups.

In a preferred embodiment of the invention, n=2, m=4, R=methyl and X=OH or OR' wherein R'=methyl or ethyl and a=1.

Within any given cyclic organosiloxane of the formula (I), each R group can be the same or different than each other group. By way of example, if m=4 and a=1, there would be two R groups attached to each of 4 Si atoms in the 4 $SiX_aR_{3-a}$ groups and one R group attached to each of the Si atoms in the 4 SiR groups. Each of these 12 R groups could be the same or different. For example, each R group attached to the Si atoms in the $SiX_aR_{3-a}$ groups could be the same as each other, but different than the R groups attached to the Si atoms in the SiR groups, which could themselves be the same as each other.

Representative cyclic organosiloxanes of the formula (I) are

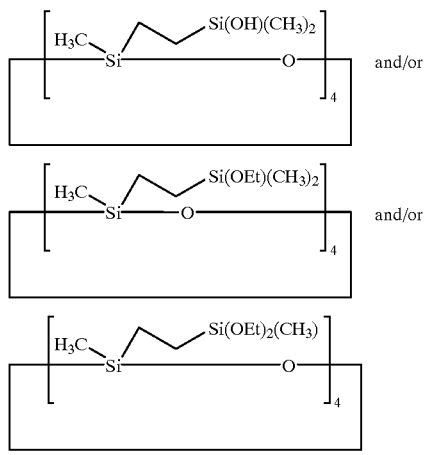

The present invention also provides a process for the production of multi-functional cyclic organosiloxanes of the formula (Ia)

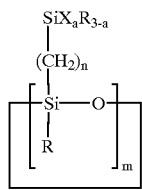

(Ia)

wherein m=3–6, preferably 3–4, a=1–3, n=2–10, preferably 2–5, particularly preferably 2, R=$C_1$–$C_8$ alkyl and/or $C_6$–$C_{14}$ aryl, preferably $C_1$–$C_2$ alkyl and wherein within the molecule each a, n and R may be identical to or different than each other a, n and R respectively, preferably identical, and wherein the remaining residues have the following meaning:

A)
X=halogen, i.e. F, Cl, Br and I, OR', preferably Cl, OR' and R' has the meaning of $C_1$–$C_8$ alkyl, preferably $C_1$–$C_2$ alkyl,
or
B)
X=[$(CH_2)_n SiY_b R_{3-b}$] with b=1–3,
and
Y=halogen, OR', preferably Cl or OR', wherein R' has the same meaning given in A),
or
C)
X=[$(CH_2)_n SiR_{3-b}[(CH_2)_n SiY_c R_{3-c}]_b$] and b=1–3, c=1–3,
and
Y=halogen, OR' or preferably Cl or OR', wherein R' has the meaning given in A)

wherein cyclic organosiloxanes of the formula (II)

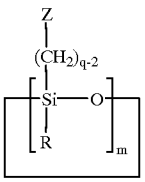

(II)

with m=3–6, preferably 3–4, R=$C_1$–$C_8$ alkyl and/or $C_6$–$C_{14}$ aryl, preferably $C_1$–$C_2$ alkyl, wherein, within the molecule, each R may be identical to or different than each other, preferably identical, and wherein the remaining residues have the following meaning:

A)
Z=$C_2H_3$ and q=2–10, preferably 2–5, particularly preferably 2,
or
B)
Z=$SiR_{3-e}(C_nH_{2n-1})_e$ with e=1–3, n=2–10, preferably 2–5, particularly preferably 2,
and
q=4–12, preferably 4–6,
or
C)
Z=$SiR_{3-e}[(CH2)_n SiR_{3-e}(C_nH_{2n-1})_e]_e$ with e=1–3, and
and
q=4–12, preferably 4–6,
n=2–10, preferably 2–5 and particularly preferably 2,
are reacted with hydridosilanes of the formula (III)

$HSiT_fR_{3-f}$ (III)

wherein f=1–3, T=halogen or OR and R=$C_1$–$C_8$ alkyl and/or $C_6$–$C_{14}$ aryl, preferably $C_1$–$C_2$ alkyl, wherein each individual R may be the same or different than each other individual R,
in the presence of heterogeneous catalysts.

In this process, cyclo(tetra(methylvinylsiloxane)), i.e. m=4, q=2, Z=$C_2H_3$ and R=methyl, is preferably used as the cyclic organosiloxane and $HSiCl_3$, $HSiCl_2Me$ or $HSiClMe_2$ as the hydridosilane.

Due to the heterogeneous catalysts used in the process according to the invention, the course of the hydrosilylation reaction and also the evolution of heat may reliably be controlled by the catalyst content. A reduced amount of catalyst leads directly to reduced evolution of heat. It is thus possible to perform the process simply on a large industrial scale.

The use of the catalyst according to the invention moreover frequently makes it unnecessary to pre-purify the educts.

A further advantage of the heterogeneous catalysts used in the industrial performance of the process according to the invention is that the hydrosilation may optionally be operated continuously, thereby considerably increasing the space/time yield.

The supported catalyst may be separated in a straightforward manner, for example, by filtration, in both continuous and discontinuous operation. The catalyst may be reused after separation in the case of discontinuous operation.

In both continuous and discontinuous operations, products are obtained which contain no catalyst residues.

Furthermore, the supported catalysts, unlike the homogeneous catalyst known in the prior art, such as for example hexachloroplatinic acid in isopropanol, may be stored without loss of activity and without special measures.

The present invention also provides a process for the production of multi-functional, cyclic organosiloxanes of the formula (Ib)

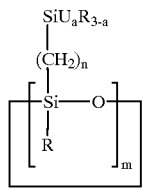
(Ib)

in which m=3–6, preferably, a=1–3, n=2–10, preferably 2–5, particularly preferably 2, R=$C_1$–$C_8$ alkyl and/or $C_6$–$C_{14}$ aryl, preferably $C_1$–$C_2$ alkyl, wherein within the molecule, a, n and R may each be identical to or different than each other a, n and R, respectively, preferably identical, and wherein the remaining residues have the following meaning:

A)
U=OR' or OH, with R'=–$C_1$–$C_8$ alkyl, preferably methyl, ethyl or

B)
U=[$(CH2)_n SiY_g R_{3-g}$] and g=1–3,
and
Y=OR' or OH, R'=$C_1$–$C_8$ alkyl, preferably methyl, ethyl, or C)
U=[$(CH_2)_n SiR_{3-g}[(CH_2)_n SiY_{3-h} R_h]_g$] and h=1–3, g=1–3
and
Y=OR' or OH, R'=$C_1$–$C_8$ alkyl, preferably methyl, ethyl,
wherein cyclic organosiloxanes of the formula (II)

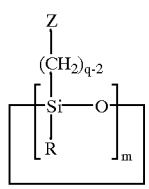
(II)

in which
m=3–6, preferably 3–4,
R=$C_1$–$C_8$-alkyl and/or $C_6$–$C_{14}$ aryl, preferably $C_1$–$C_2$ alkyl, and wherein, within the molecule, each R may be identical to or different than each other, preferably identical, and wherein the remaining residues have the following meaning:

A)
Z=$C_2H_3$ and
q=2–10, preferably 2–5, particularly preferably 2, or

B)
Z=$SiR_{3-b}(C_nH_{2n-1})_b$ with b=1–3 wherein within the molecule each b may be identical to or different, than each other b, preferably identical, n=2–10, preferably 2–5, particularly preferably 2 and
q=4–12, preferably 4–6, or C)
Z=$SiR_{3-b}[(CH_2)_n SiR_{3-b}(C_n H_{2n-1})_b]_b$ and with b=1–3, wherein within the molecule, each b may be identical to or different than each other b, preferably identical, n=2–10, preferably 2–5, particularly preferably 2 and
q=4–12, preferably 4–6 are reacted with hydridosilanes of the formula (III)

$$HSiT_f R_{3-f} \quad \text{(III)}$$

in which f=1–3, T=halogen, in the presence of heterogeneous catalysts and are then hydrolyzed with water or alcoholyzed with an alcohol.

The heterogeneous catalyst is preferably platinum or a platinum compound applied onto the most varied support materials. Materials based on carbon or metal oxides or oxide mixtures may be mentioned as examples of support materials. The support materials may be of synthetic or natural origin, ie. they may consist, for example, be clay minerals, pumice, kaolin, bleaching earths, bauxites, bentonites, diatomaceous earth, asbestos or zeolite. In a preferred embodiment of the invention, the catalytically active constituent is applied onto a carbonaceous support, such as for example activated carbon, carbon black, graphite or coke. Activated carbon is particularly preferred in this connection.

The supported catalyst may be used in pulverulent form as well as in the form of shapes, for example as spheres, cylinders, rods, hollow cylinders or rings.

The catalyst used in the process according to the invention is preferably applied onto a suitable support. The reactive component of the catalyst when in the reactive state is preferably a platinum halide or a complex compound containing a platinum halide, which may moreover contain, for example, olefins, amines, phosphines, nitrites, carbon monoxide or water, such as for example $A_2PtCl_6$, wherein A denotes, for example, H, Li, Na, K, $NH_4$, Rb, Cs, $NR_4$ with R in $NR_4$ being an organic residue $C_6$ to $C_{10}$ aryl, $C_7$ to $C_{12}$ aralkyl and/or a $C_1$ to $C_{20}$ alkyl residue of, and Hal denotes a halogen, such as for example F, Cl, Br or I. Such halogen-containing platinum complex compounds are known in the art.

In a preferred embodiment of the invention, the catalyst used in the process according to the invention is produced in situ. To this end, the platinum halide or the complex compound containing platinum halide is produced in situ on the support during preparation from a suitable halogen-free platinum metal compound and a compound containing halide. Halogen-free platinum metal compounds which may be used are, for example, platinum nitrate, oxide, hydroxide, acetylacetonate and others which are known to the person skilled in the art. Compounds containing halide which may be used are salts containing halogen and complex compounds of the elements of main groups 1 to 3 and subgroups 1 to 8 of the periodic system of elements (Mendeleyev) together with the rare earth metals (atomic numbers 58–71). Examples are NaBr, NaCl, $MgBr_2$, $AlCl_3$, $NaPF_6$, $MnCl_2$, $CoBr_2$, $CeCl_3$, $SmI_2$, $CuCl_2$, $Na_2ZnCl_4$, $TiCl_4$.

The quantity of the platinum halide or of the complex compound containing the platinum halide in the reactive state is preferably 0.01 to 15 wt. %, particularly preferably 0.05 to 10 wt. %, calculated as metallic platinum and relative to the total weight of the catalyst.

Suitable solvents for the production of supported catalysts according to the invention which may be mentioned are, for example, water, aliphatic hydrocarbons, such as pentane, n-hexane, cyclohexane, etc., aliphatic halogenated hydrocarbons, such as dichloromethane, trichloromethane, etc., aromatic hydrocarbons, such as benzene, toluene, xylene, etc., halogenated aromatic hydrocarbons, such as chlorobenzene, dichlorobenzene, etc., primary, secondary or tertiary alcohols, such as methanol, ethanol, n-propanol, iso-propanol, n-butanol, iso-butanol, t-butanol, cumyl alcohol, iso-amyl alcohol, diethylene glycol, etc., ketones, such as acetone, 2-butanone, methyl isobutyl ketone, acetyl acetone, etc., ethers, such as diethyl ether, diisopropyl ether, methyl t-butyl ether, dioxane, tetrahydrofuran etc., esters, such as methyl acetate, ethyl acetate, etc., nitrites, such as acetonitrile, benzonitrile, etc., carbonates, such as dimethyl carbonate, diethyl carbonate, diphenyl carbonate etc., dimethylacetamide, N-methylpyrrolidinone and tetramethylurea. Mixtures of such solvents may, of course, also be used.

The catalyst to be used according to the invention is produced using methods which are known to those skilled in the art. Solutions containing platinum and the stated compounds containing halide may thus be applied onto the catalyst support to be used according to the invention by soaking, adsorption, immersion, spraying, impregnation and ion exchange. It is also possible to attach platinum and the stated compounds containing halide onto the support using a base. Bases which may be considered are, for example, NaOH, $Li_2CO_3$ and potassium phenolate. Platinum and the compound containing halide may be applied onto the support both in any desired sequence and simultaneously.

When applying the platinum by soaking with a solution containing platinum, the duration of soaking is slightly dependent upon the platinum compound used, the shape and porosity of the support used and the solvent. The duration generally ranges from a several minutes to several hours, preferably from 0.01 to 30 hours, particularly preferably from 0.05 to 20 hours, very particularly preferably from 0.1 to 15 hours.

The mixture may be stirred during soaking. It may, however, also be advantageous to allow the mixture to stand or to shake it, so that any optionally used shapes are not damaged by a stirrer.

After soaking, the supported catalyst may be separated, for example by filtration, settling or centrifugation. Excess solvent may here be removed, for example, by distillation.

After soaking, the resultant supported catalysts are preferably dried. This may proceed in air, under a vacuum or in a stream of gas. Preferred gases for drying the supported catalyst in a stream of gas are, for example, nitrogen, oxygen, carbon dioxide or noble gases together with any desired mixtures of the stated gases, preferably, for example, air. Drying preferably proceeds at 20 to 200° C., particularly preferably at 40 to 180° C., very particularly preferably at 60 to 150° C.

Drying time is dependent, for example, on the porosity of the support used and on the solvent used. It preferably ranges from 0.5 to 50 hours, particularly preferably from 1 to 40 hours, very particularly preferably from 1 to 30 hours.

After drying, the dried supported catalysts may be calcined. This may proceed in air, under a vacuum or in a stream of gas. Preferred gases for calcining the supported catalyst in a stream of gas are, for example, nitrogen, oxygen, carbon dioxide or noble gases together with any desired mixtures of the stated gases, preferably, for example, air. Calcination preferably proceeds at 100 to 800° C., particularly preferably at 100 to 700° C., very particularly preferably at 100 to 600° C.

Calcination time preferably ranges from 0.5 to 50 hours, particularly preferably from 1 to 40 h, very particularly preferably from 1 to 30 hours.

The supported catalysts may be used in the form of powders or shapes e.g. spheres, cylinders, rods, hollow cylinders or rings, and be separated from the reaction mixture for example by filtration, settling or centrifugation.

The compounds of the formula II)A) are, for example, obtainable from methylvinyldichlorosilane by conventional hydrolysis and subsequent fractionation processes.

Compounds of the formula (II)B) can be synthesized, as described in Organometallics 1994, 13, 2682, starting from compounds of the formula (II)A) and hydrosilation with hydridosilanes, for example $HSiCl_3$, $HSiCl_2Me$ or $HSiClMe_2$. These reaction products are then further reacted with for example alkenylmagnesiumhalides to obtain the compounds (II)B). In a similar manner, compounds (II)C) are obtained starting with (II)B).

The present invention additionally provides the use of the multi-functional, cyclic organosiloxanes according to the invention as crosslinking agents in condensation-crosslinking organopolysiloxane compositions and for the production or modification of surface coating compositions.

The invention is illustrated by, but not limited to, the following examples.

PRACTICAL EXAMPLES

Preliminary note:

With the exception of catalyst preparation, all reactions were performed under a nitrogen atmosphere or a vacuum in reaction apparatus consisting of a multi-necked flask with a gas inlet, jacketed coil condenser with bubble counter and mechanical stirrer. Unless otherwise stated, all the solvents used were dried by conventional laboratory methods before use and used in distilled form under nitrogen. Commercial educts, such as chlorodimethylsilane and cyclo(tetra (methylvinylsiloxane)), were used without further purification.

$^1$H-NMR spectra were recorded using a Bruker AMX 500.

EXAMPLE 1

Surface modification of pulverulent activated carbon with $H_2PtCl_6$ (Cat I)

49.5 g of Norit® CN 1 (specific surface area 1400 m$^2$/g and particle size 75 μm (10–20%)) activated carbon were suspended in 300 ml of twice distilled water and combined with 200 ml of an aqueous $H_2PtCl_6$ solution which contained 0.5 g of Pt, calculated as elemental metal. The mixture was stirred for 10 minutes and the catalyst filtered out using a Buchner funnel. The moist crude product (153 g) was dried at 0.1 Pa and 110° C. and stored under argon. The resulting catalyst (catalyst Cat I) contained 1% of Pt by weight of catalyst.

EXAMPLE 2

Surface modification of activated carbon shapes with $H_2PtCl_6$ (Cat II)

49.5 g (114.6 ml) of Norit ROX® 0.8 (specific surface area 1000 m$^2$/g and average particle size 0.8 mm) extruded activated carbon shapes were soaked with 33.9 ml of an aqueous $H_2PtCl_6$ solution which contained 0.5 g of Pt, calculated as metal. The crude product was dried first at 110° C. in a stream of nitrogen, then dried at 0.1 Pa and 110° C. and stored under nitrogen. The catalyst contained 1% of Pt.

EXAMPLE 3

Surface modification of pulverulent $SiO_2$ with $H_2PtCl_6$ (Cat III)

49.5 g of $SiO_2$ having a specific surface area of 180 m$^2$/g (Merck 657®) were worked to a paste with 132 ml of an aqueous $H_2PtCl_6$ solution which contained 0.5 g of Pt, calculated as metal. The moist crude product is dried first at 110° C. in a drying cabinet, then dried at 0.1 Pa and 110° C. and stored under argon. The catalyst contained 1% of Pt by weight of catalyst.

EXAMPLE 4

Surface modification of pulverulent $Al_2O_3$ with $H_2PtCl_6$ (Cat IV)

49.5 g of γ-$Al_2O_3$ having a specific surface area of 250 m$^2$/g (Rhône-Poulenc, SPH 509®) were worked to a paste with 40 ml of an aqueous $H_2PtCl_6$ solution which contained 0.5 g of Pt, calculated as metal. The moist crude product was dried first at 110° C. in a drying cabinet, then dried at 0.1 Pa and 110° C. and stored under argon. The catalyst contained 1% of Pt by weight of catalyst.

EXAMPLE 5

Surface modification of pulverulent $TiO_2$ with $H_2PtCl_6$ (Cat V)

49.5 g of $TiO_2$ having a specific surface area of 330 m$^2$/g (Bayer PK 5 585®) were worked to a paste with 70 ml of an aqueous $H_2PtCl_6$ solution which contained 0.5 g of Pt, calculated as elemental metal. The moist crude product was dried first at 110° C. in a drying cabinet, then dried at 0.1 Pa and 110° C. and stored under argon. The catalyst contained 1% of Pt by weight of catalyst.

EXAMPLE 6

Synthesis of cyclo{SiO(CH$_3$)[(CH$_2$)$_2$SiCl(CH$_3$)$_2$]}$_4$ 69 g (726.7 mmol) of chlorodimethylsilane were added to a stirred mixture of 50 g (145.2 mmol) of cyclo{SiO(CH$_3$)(C$_2$H$_3$)}$_4$ and 800 mg of catalyst Cat I in 120 ml of THF. The reaction mixture was heated to 50° C., no evolution of heat being observed even after 2 h at this temperature. After a further 20 h at 55 to 60° C., the mixture was cooled to room temperature and the catalyst filtered out through a reverse sintered filter. Volatile constituents were removed from the clear, colorless filtrate under a vacuum and the product was obtained as a colorless oil which was found to have the emperical formula $C_{20}H_{52}Cl_4Si_8O_4$ M=723.127 g/mol $^1$H-NMR: (CDCl$_3$)

δ=0.09 ppm (s, 3H, O$_2$Si(C$\underline{H}$$_3$)(CH$_2$)$_2$Si(CH$_3$)$_2$Cl); 0.39 ppm (s, 6H, Si(CH$_3$)$_2$Cl); 0.51 ppm and 0.74 ppm (m, in each case 2H, Si(CH$_2$)$_2$Si).

EXAMPLE 7

Synthesis of cyclo{SiO(CH$_3$)[(CH$_2$)$_2$Si(OH)(CH$_3$)$_2$]}$_4$ 105 g (145.5 mmol) of cyclo{SiO(CH$_3$)[(CH$_2$)$_2$SiCl(CH$_3$)$_2$]}$_4$ in 100 ml of diethyl ether were added dropwise with stirring over the course of one hour to a mixture consisting of 87.4 ml (63.6 g; 628.3 mmol) of triethylamine, 12.1 ml (12.1 g; 672.2 mmol) of water and 2850 ml of tert.-butyl methyl ether. On completion of addition, stirring was continued for a further hour and the triethylamine hydrochloride precipitate was then filtered out. The volatile constituents were then removed under a vacuum using a rotary evaporator, the oily residue was redissolved in a little THF and filtered through silica gel. Once all volatile constituents had again been removed under a vacuum, the product was obtained as a viscous oil.

Yield: 69.5 g, corresponding to 74% of theoretical.

Emperical formula: $C_{20}H_{56}Si_8O_8$

M=649.346 g/mol $^1$H-NMR: (DMSO-d$_6$)

δ=0.06 ppm (s, 9H, SiCH$_3$); 0.42 ppm (m, 4H, SiCH$_2$); 5.27 ppm (s, 1H, SiOH).

EXAMPLE 8

Reaction of cyclo-[SiOMe((CH$_2$)$_2$SiMe$_2$Cl)]$_4$ with ethanol 36 g of ethanol were slowly stirred over a period of 1 hour into 72 g (0.1 mol) of the compound produced in Example 6 [OSiMe((CH$_2$)$_2$SiMe2Cl)]$_4$. On completion of addition, the mixture was refluxed for 1 hour at a pressure of 250 mbar. The specimen was then conditioned to 100° C./250 mbar and neutralised. The mixture was stirred for 1 hour at room temperature, the precipitate filtered out and conditioned to 100° C./20 mbar. The product took the form of a colourless liquid.

Yield: 71.5 g, corresponding to 94.4% of theoretical

Molecular weight: 760 g/mol

Viscosity η$_($23° C.)=240 mPa.s (25° C.); density ρ$_($23° C.)=0.960 g/cm$^3$

EXAMPLE 9

Synthesis of cyclo-{SiOMe[CH$_2$CH$_2$SiMe$_2$(OMe)]}$_4$ 100 g of cyclo-[SiOMe(CH$_2$CH$_2$SiMe2Cl)]$_4$ produced as described in example 6 and 200 g of tert.-butylmethylether were placed in 1 liter flask equipped with a stirrer and an external cooling device. 40 g of methanol were added to the stirred solution over a period of 1 hour and 25 minutes. After the end of the addition process, stirring was continued for 30 minutes at a temperatur 40° C. and a pressure of 250 mbar. The mixture was allowed to cool to ambient temperature. At atmospheric pressure ammonia gas was bubbled through the solution until the mixture tested alkaline. The NH$_4$Cl precipitate was filtered off and the filtrate was distilled under reduced pressure up to a temperature of 80° C.

Yield: 92 g of a clear liquid with a viscosity of 48 mPa.s.

C$_{24}$H64Si$_8$O$_8$

M=704 gmol$^{-1}$ $^1$H-NMR (CDCl$_3$):

δ=0.09 ppm (s, 9H, OSiC$\underline{H}$$_3$—CH$_2$CH$_2$Si(C$\underline{H}$$_3$)$_2$(OCH$_3$);

δ=0.42 ppm (m, 4H, OSiCH$_3$—C$\underline{H}$$_2$C$\underline{H}$$_2$Si(CH$_3$)$_2$(OCH$_3$));

δ=3.4 ppm (m, 3H, OSiCH$_3$—CH$_2$CH$_{2,n}$Si(CH$_3$)$_2$(OC$\underline{H}$$_3$)).

EXAMPLE 10

Formation of an organic-inorganic hybridmaterial with cyclo-[SiOMe((CH$_2$)$_2$Si(OMe)Me$_2$)]$_4$ and use as coating 4.25 g (6.02 mmol) of cyclo-[SiOMe((CH$_2$)$_2$Si(OMe)Me$_2$)]$_4$, 7.5 g (8.1 ml; 36.1 mmol) of tetraethylorthosilicate, 10 ml of ethanol, 1.5 g of 0.1 N HCl were mixed and stirred 20 hours. Then, the transparent, colorless coating solution was brought onto a glass plate using a film casting frame (120 μm wet film thickness). After about 10 min drying at room temperature, the coating was cured 15 min at 160° C.

in an oven. After cooling to room temperature a transparent, homogeneous and crackfree film was obtained.

What is claimed is:

1. Process for the production multi-functional, cyclic organosiloxanes of the formula (I),

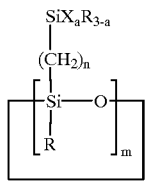
(I)

in which m=3–6, n=2–10, R=$C_1$–$C_8$ alkyl, or $C_6$–$C_{14}$ aryl, wherein, within the molecule, each n and each R may be identical to or different than each other n or R and wherein the remaining residues have the following meaning:

A)
   X=halogen and a=1–3
   or X=OR' or OH, a=1–2 and R' has the meaning of $C_1$–$C_8$ alkyl,
or
B)
   X=$[(CH_2)_nSiY_bR_{3-b}]$ a=1–3 and b=1–3 and
   Y=halogen, OR' or OH and R' has the meaning of $C_1$–$C_8$-alkyl
or
C)
   X=$[(CH_2)_nSiR_{3-b}[(CH_2)_nSiY_cR_{3-c}]_b]$, a=1–3 and b=1–3 and c=1–3 and
   Y=halogen, OR' or OH and R' has the meaning of $C_1$–$C_8$-alkyl
whereby cyclic organosiloxanes of the formula (II)

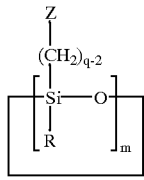
(II)

in which m=3–6, R=$C_1$–$C_8$ alkyl or $C_6$–$C_{14}$ aryl, wherein, within the molecule, each individual R may be identical or different from each other individual R, and wherein the remaining residues have the following meaning:

A)
   Z=$C_2H_3$ and q=2–10
or
B)
   Z=$SiR_{3-e}(C_nH_{2n-1})_e$ with e=1–3, and n=2–10, wherein, within the molecule each individual e may be identical or different from each other individual e and q=4–12
or
C)
   Z=$SiR_{3-e}[(CH_2)_nSiR_{3-e}(C_nH_{2n-1})_e]_e$ with e=1–3, wherein, within the molecule, each individual e may be identical or different from each other individual e, q=4–12
   and n=2–10
are reacted with hydridosilanes of the formula (III)

$HSiT_fR_{3-f}$ (III)

in which f=1–3, T=halogen or OR', and R'=$C_1$–$C_8$ alkyl or $C_6$–$C_{14}$ aryl, wherein each individual R' may be the same or different than each other individual R',
   in the presence of a heterogeneous catalyst.

2. A method of condensation-crosslinking organopolysiloxane compositions which comprises crosslinking said organopolysiloxane compositions with a cyclic organosiloxane of the formula (I),

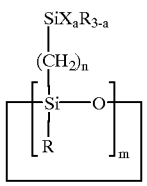
(I)

in which m=3–6, n 2–10, R=$C_1$–$C_8$ alkyl, or $C_6$–$C_{14}$ aryl, wherein, within the molecule, each n and each R may be identical to or different than each other n or R and wherein the remaining residues have the following meaning:

A)
   X=halogen and a=1–3
   or X=OR' or OH, a=1–2 and R' has the meaning of $C_1$–$C_8$ alkyl,
or
B)
   X=$[(CH_2)_nSiY_bR_{3-b}]$ a=1–3 and b=1–3 and
   Y=halogen, OR' or OH and R' has the meaning of $C_1$–$C_8$-alkyl
or
C)
   X=$[(CH_2)_nSiR_{3-b}[(CH_2)_nSiY_cR_{3-c}]_b]$, a=1–3 and b=1–3 and c=1–3 and
   Y=halogen, OR' or OH and R' has the meaning of $C_1$–$C_8$-alkyl.

3. Multi-functional, cyclic organosiloxanes of the formula (I),

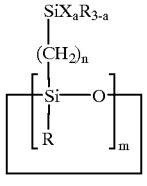
(I)

in which m=3–6, n=2–10, R=$C_1$–$C_8$ alkyl, or $C_6$–$C_{14}$ aryl, wherein within the molecule, each n and each R may be identical to or different than each other n or R and wherein the remaining residues have the following meaning:

A)
   X=OH, a=1–2
or
B)
   X=$[(CH_2)_nSiY_bR_{3-b}]$ a=1–3 and b=1–3 and
   Y=halogen, OR' or OH and R' has the meaning of $C_1$–$C_8$-alkyl
or
C)
   X=$[(CH_2)_nSiR_{3-b}[(CH_2)_nSiY_cR_{3-c}]_b]$, a=1–3 and b=1–3 and c=1–3 and Y=halogen, OR' or OH and R' has the meaning of $C_1$–$C_8$-alkyl.

4. Multi-functional, cyclic organosiloxanes according to claim 3, wherein n=2, m=4, X=OH, R'=methyl or ethyl and a=1.

5. Process according to claim 1, wherein cyclo(tetra(methylvinylsiloxane)) is used as the cyclic organosiloxane and $HSiCl_3$, $HSiCl_2Me$ or $HSiClMe_2$ as the hydridosilane.

6. Process for the production of multi-functional, cyclic organosiloxanes of the formula (Ib),

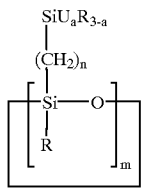

(Ib)

in which m=3–6, a=1–3, n=2–10, R=$C_1$–$C_8$ alkyl or $C_6$–$C_{14}$ aryl, wherein, within the molecule, each individual a, n and R may be identical to or different than each other individual a, n and R, and wherein the remaining residues have the following meaning:

A)
   U=OR' or OH, with R'=$C_1$–$C_8$ alkyl
or
B)
   U=[$(CH_2)_n SiY_g R_{3-g}$] with g=1–3,
   and
   Y=OR' or OH, with R'=$C_1$–$C_8$ alkyl
or
C)
   U=[$(CH_2)_n SiR_{3-g}$[$(CH_2)_n SiY_h R_{3-h}$]$_g$] with h=1–3, g=1–3,
   Y=OR' or OH, with R'=$C_1$–$C_8$ alkyl,
wherein cyclic organosiloxanes of the formula (II)

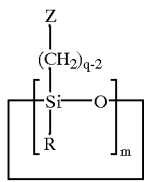

(II)

in which m=3–6, R=$C_1$–$C_8$ alkyl or $C_6$–$C_{14}$ aryl, wherein, within the molecule, each individual R may be identical to or different than each other individual R, and wherein the remaining residues have the following meaning:

A)
   Z=$C_2H_3$ with q=2–10
or
B)
   Z=$SiR_{3-b}(C_nH_{2n-1})_b$ with b=1–3, wherein, within the molecule, each individual b may be identical to or different than each other individual b, q=4–12 and n=2–10.

or
C)
   Z=$SiR_{3-b}$[$(CH_2)_n SiR_{3-b}(C_nH_{2n-1})_b$]$_b$ with b=1–3, wherein, within the molecule, each individual b may be identical to or different than each other individual b, q=4–12 and n=2–10.

are reacted with hydridosilanes of the formula (III)

$$HSiT_fR_{3-f} \quad\quad\quad (III)$$

with f=1–3, T=halogen,
in the presence of a heterogeneous catalyst and are then hydrolyzed with water or alcoholyzed with an alcohol.

7. Process according to claim 1, wherein the heterogeneous catalyst is platinum or a platinum compound as catalytically active constituent on carbon as a support material.

8. Process according to claim 1, wherein hexachloroplatinic acid on activated carbon is used as the heterogeneous catalyst.

9. Process according to claim 1, wherein the reaction proceeds discontinuously in a solvent.

10. A multi-functional cyclic organosiloxane of the formula (I) wherein said organosiloxane is cyclo-{$SiO(CH_3)$[$(CH_2)_2Si(OH)(CH_3)_2$]}$_4$.

11. Surface coating agents comprising multi-functional, cyclic organosiloxanes of the formula (I),

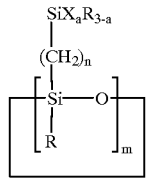

(I)

in which m=3–6, n=2–10, R=$C_1$–$C_8$ alkyl, or $C_6$–$C_{14}$ aryl, wherein, within the molecule, each n and each R may be identical to or different than each other n or R and wherein the remaining residues have the following meaning:

A)
   X=halogen and a=1–3
   or X=OR' or OH, a=1–2 and R' has the meaning of $C_1$–$C_8$ alkyl,
or
B)
   X=[$(CH_2)_n SiY_b R_{3-b}$] a=1–3 and b=1–3 and
   Y=halogen, OR' or OH and R' has the meaning of $C_1$–$C_8$-alkyl
or
C)
   X=[$(CH_2)_n SiR_{3-b}$[$(CH_2)_n SiY_c R_{3-c}$]$_b$], a=1–3 and b=1–3 and c=1–3 and
   Y=halogen, OR' or OH and R' has the meaning of $C_1$–$C_8$-alkyl.

* * * * *